US00PP19159P2

(12) United States Plant Patent
Trees

(10) Patent No.: US PP19,159 P2
(45) Date of Patent: Aug. 26, 2008

(54) ***BIDENS* PLANT NAMED 'BALBIDSUKI'**

(50) Latin Name: *Bidens ferulifolia*
Varietal Denomination: Balbidsuki

(75) Inventor: Scott C. Trees, Guadalupe, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/973,971

(22) Filed: Oct. 11, 2007

Related U.S. Application Data

(60) Provisional application No. 60/874,444, filed on Dec. 12, 2006.

(51) Int. Cl.
*A01H 5/00* (2006.01)

(52) U.S. Cl. ..... Plt./410

(58) Field of Classification Search ..... Plt./410
See application file for complete search history.

(56) References Cited

PUBLICATIONS

Canada Plant Breeders' Rights application No. 06–5283 filed Mar. 9, 2006. Published information from Canada Plant Breeders' Rights Office web site attached.
European Plant Breeders' Rights No. 20934 granted Sep. 24, 2007. Certificate and published information from the Community Plant Variety Office web site attached.
Plant material first became available to the public on Feb. 25, 2006 as the result of a United States sale.

*Primary Examiner*—Annette H Para
(74) *Attorney, Agent, or Firm*—Audrey Charles

(57) ABSTRACT

A new and distinct cultivar of *Bidens* plant named 'Balbidsuki', characterized by its golden yellow-colored flowers, medium green-colored foliage, and minimally vigorous, compact, and mounded growth habit.

1 Drawing Sheet

Latin name of genus and species of plant claimed: *Bidens ferulifolia.*
Variety denomination: 'Balbidsuki'.

BACKGROUND OF THE INVENTION

The present invention relates to a new and distinct cultivar of *Bidens* plant botanically known as *Bidens ferulifolia* and hereinafter referred to by the cultivar name 'Balbidsuki'.

The new cultivar originated in a controlled breeding program in Arroyo Grande, Calif. during July 2004. The objective of the breeding program was the development of *Bidens* cultivars with dark green-colored foliage and a compact to vigorous growth habit.

The new cultivar is the result of open-pollination. The female (seed) parent of the new cultivar is Solaire 'Bidtis-1', U.S. Plant Pat. No. 12,280, characterized by its golden yellow-colored flowers, medium green-colored foliage, and compact-upright growth habit. The male (pollen) parent of the new cultivar is unknown. The new *Bidens* cultivar was discovered and selected as a single flowering plant within the progeny of the above stated open-pollination during November 2004 in a controlled environment at Arroyo Grande, Calif.

Asexual reproduction of the new cultivar by terminal stem cuttings since November 2004 at Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balbidsuki' as a new and distinct cultivar of *Bidens* plant:

1. Golden yellow-colored flowers;
2. Medium green-colored foliage; and
3. Minimally vigorous, compact, and mounded growth habit.

Plants of the new cultivar differ from plants of the female parent primarily in growth habit. Plants of the new cultivar were selected as being more compact than the female parent.

While the female parent, Solaire 'Bidtis-1', is similar in comparison to the new cultivar, plants were not commercially available for a side by side comparison. Based on information in U.S. Plant Pat. No. 12,280, plants of the new cultivar differ from plants of 'Bidtis-1' in the following characteristics:

1. Plants of the new cultivar have a stem color different from plants of 'Bidtis-1';
2. Plants of the new cultivar have a disc floret color different from plants of 'Bidtis-1'; and
3. Plants of the new cultivar have slightly wider leaves than plants of 'Bidtis-1'.

Of the many commercially available *Bidens* cultivars known to the inventor, the most similar in comparison to the new cultivar is 'Golden Star', U.S. Plant Pat. No. 12,589. However, in side by side comparisons, plants of the new cultivar differ from plants of 'Golden Star' in the following characteristics:

4. Plants of the new cultivar are narrower than plants of 'Golden Star';
5. Plants of the new cultivar have smaller leaves than plants of 'Golden Star'; and
6. Plants of the new cultivar have smaller flowers than plants of 'Golden Star'.

In addition, plants of the new cultivar are similar in comparison to 'California Sun', not patented. However, in side by side comparisons, plants of the new cultivar differ from plants of 'California Sun' in the following characteristics:

1. Plants of the new cultivar are narrower than plants of 'California Sun'; and
2. Plants of the new cultivar have smaller flowers than plants of 'California Sun'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balbidsuki'. The plants were grown in 4.5 inch pots for 7 weeks in a greenhouse at West Chicago, Ill.

DETAILED BOTANICAL DESCRIPTION

Figure 1:
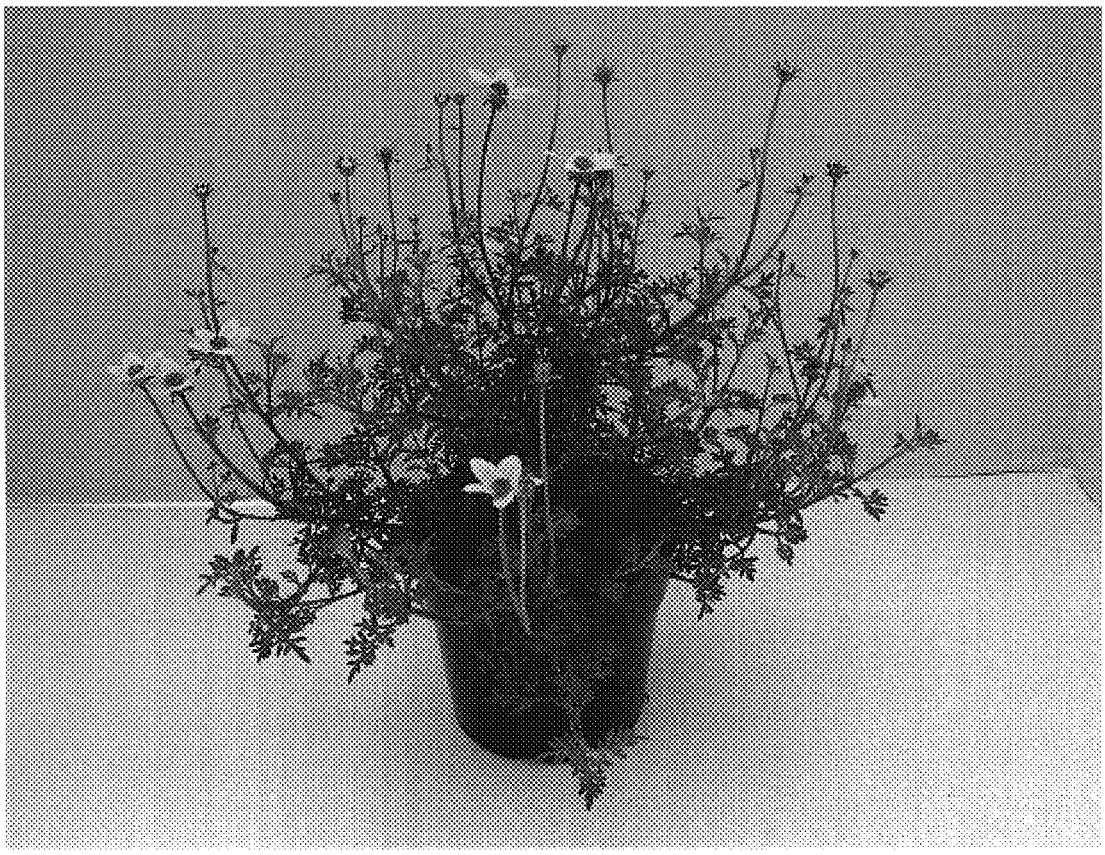
FIG. 1 illustrates a side view of the overall growth and flowering habit of 'Balbidsuki'.
Figure 2:
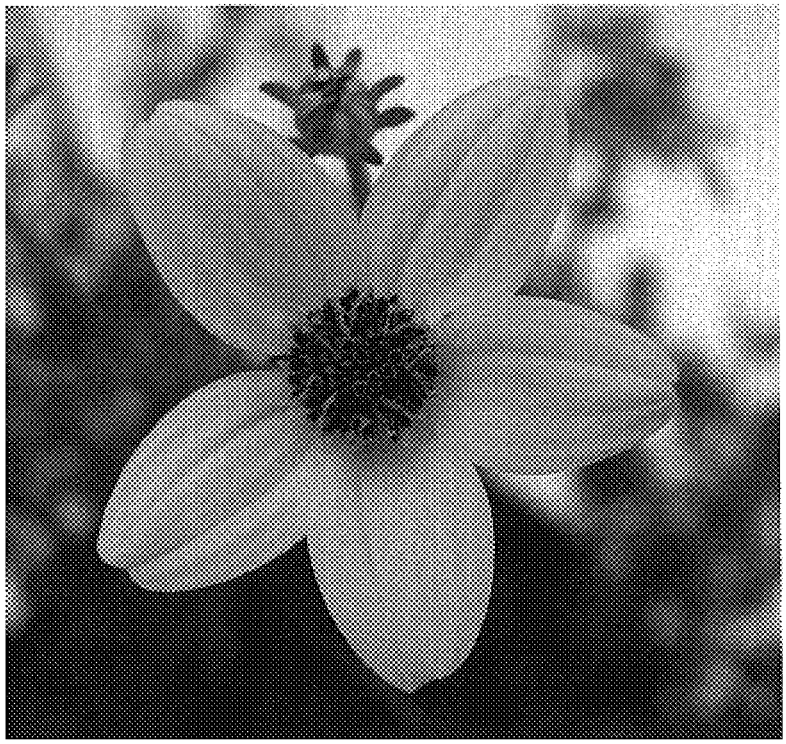
FIG. 2 illustrates a close-up view of an individual inflorescence of 'Balbidsuki'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Jun. 20, 2006 between 9:00 a.m. and 11:00 a.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 7 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Bidens ferulifolia* cultivar Balbidsuki.

Parentage:

*Female parent.*—Solaire 'Bidtis-1', U.S. Plant Pat. No. 12,280.

*Male parent.*—Unknown.

Propagation:

*Type cutting.*—Terminal stem.

*Time to initiate roots.*—Approximately 5 to 7 days.

*Time to produce a rooted cutting.*—Approximately 21 to 24 days.

*Root description.*—Fibrous.

*Rooting habit.*—Freely branching.

Plant description:

*Commercial crop time.*—Approximately 5 to 7 weeks from a rooted cutting.

*Growth habit and general appearance.*—Minimally vigorous, compact, and mounded.

*Size.*—Height from soil level to top of plant plane: Approximately 20.9 cm. Width: Approximately 31.2 cm.

*Branching habit.*—Freely branching. Quantity of main branches per plant: Approximately 5.

*Branch.*—Strength: Strong. Length: Approximately 23.0 cm. Diameter: Approximately 3.4 mm. Length of central internode: Approximately 2.5 cm. Texture: Densely pubescent. Color of young stem: 145B. Color of mature stem: 145B with overlay of 187B.

Foliage description:

*General description.*—Quantity of leaves per main branch: Approximately 17. Fragrance: None. Form: Simple. Arrangement: Opposite.

*Leaves.*—Aspect: Acute angle to stem; perpendicular to obtuse angle to stem with age. Shape: Ovate. Margin: Deeply bipinnatifid. Apex of divisions: Acuminate. Base of divisions: Attenuate. Venation pattern: Pinnate. Length of mature leaf: Approximately 2.6 cm. Width of mature leaf: 2.5 cm. Texture of upper and lower surfaces: Sparsely pubescent with densely pubescent venation. Color of upper surface of young foliage: 138A with venation of 138A. Color of lower surface of young and mature foliage: 138B with venation of 138B. Color of upper surface of mature foliage: 137B with venation of 137B.

*Petiole.*—Length: Approximately 8.8 mm. Diameter: Approximately 2.0 mm. Texture: Densely pubescent. Color: 138B with overlay of 187B.

Flowering description:

*Flowering habit.*—'Balbidsuki' is freely flowering under outdoor growing conditions with substantially continuous blooming from spring through autumn and year-round in greenhouse environment.

*Lastingness of individual inflorescence on the plant.*—Approximately 9 to 11 days.

Inflorescence description:

*General description.*—Type: Daisy-type composite, actinomorphic. Persistent. Shape: Round. Aspect: Slightly concave. Arrangement: Above the foliage. Disc and ray florets arranged acropetally on a capitulum. Quantity per plant: Approximately 10. Diameter: Approximately 2.8 cm. Depth: Approximately 6.4 mm. Fragrance: None.

*Peduncle.*—Strength: Strong. Aspect: Erect, arising from leaf axils. Length: Approximately 6.7 cm. Diameter: Approximately 1.5 mm. Texture: Densely pubescent. Color: 146B with an overlay at base of 187B.

*Bud.*—Rate of opening: Generally takes 4 to 5 days for bud to progress from first color to fully open flower. Quantity per plant: Approximately 8.

*Bud just before opening.*—Shape: Oblate. Diameter: Approximately 4.2 mm. Color: 154C.

*Ray florets.*—Quantity per inflorescence: Approximately 5. Arrangement: Imbricate in a single whorl. Aspect: Slightly concave. Shape: Ovate. Margin: Entire. Apex: Retuse. Base: Rounded. Length: Approximately 1.4 cm. Width: Approximately 8.3 mm. Texture of upper surface: Glabrous. Texture of lower surface: Glabrous, ribbed. Color of upper surface when first open: 13A. Color of lower surface when first open: 13B. Color of upper surface when fully open: 12A. Color of lower surface when fully open: 12B.

*Disc florets.*—Quantity per inflorescence: Approximately 70. Arrangement: Massed in center of inflorescence. Shape: Tubular. Margin: Entire. Apex: Five acute tips. Base: Attenuate, fused. Length: Approximately 7.0 mm. Diameter at apex: Approximately 1.0 mm. Diameter at base: Approximately 1.0 mm. Texture: Glabrous. Color when first and fully open: 14B, transparent.

*Disc.*—Diameter: Approximately 7.2 mm. Depth: Approximately 4.0 mm.

*Receptacle.*—Shape: Concave. Height: Approximately 2.0 mm. Diameter at apex: Approximately 4.0 mm. Color: 145C.

*Phyllaries.*—Quantity per inflorescence Approximately 8. Arrangement: In a single whorl. Shape: Obelliptic. Margin: Entire. Apex: Acute. Base: Truncate. Length: Approximately 4.0 mm. Width: Approximately 2.0 mm. Texture of upper surface: Sparsely pubescent. Texture of lower surface: Glabrous. Color of upper surface: 137A. Color of lower surface: 137B.

*Reproductive organs.*—Androecium: Present on disc florets only. Stamen quantity: 5 per floret. Stamen length: Approximately 5.0 mm. Anther shape: Linear. Anther length: Approximately 2.0 mm. Anther color: 200A. Pollen amount: Moderate. Pollen color: 16A. Gynoecium: Present on ray and disc florets. Pistil quantity: 1 per floret. Pistil length: Approximately 7.0 mm. Stigma shape: Two-parted. Stigma length: Approximately 1.0 mm. Stigma color: 15A. Style length: Approximately 5.0 mm. Style color: 154D, transparent. Ovary length: Approximately 1.0 mm. Ovary color: 145C.

Seed and fruit production: Neither seed nor fruit production has been observed.

Disease and pest resistance: Resistance to pathogens and pests common to *Bidens* has not been observed.

What is claimed is:

1. A new and distinct cultivar of *Bidens* plant named 'Balbidsuki', substantially as herein shown and described.

* * * * *